United States Patent
Al-Ali et al.

(10) Patent No.: US 10,092,200 B2
(45) Date of Patent: *Oct. 9, 2018

(54) PLETHYSMOGRAPH VARIABILITY PROCESSOR

(71) Applicant: Masimo Corporation, Irvine, CA (US)

(72) Inventors: Ammar Al-Ali, Tustin, CA (US);
Walter Weber, Laguna Hills, CA (US);
Anmol Majmudar, Irvine, CA (US)

(73) Assignee: Masimo Corporation, Irvine, CA (US)

( * ) Notice: Subject to any disclaimer, the term of this patent is extended or adjusted under 35 U.S.C. 154(b) by 1002 days.

This patent is subject to a terminal disclaimer.

(21) Appl. No.: 13/858,249

(22) Filed: Apr. 8, 2013

(65) Prior Publication Data

US 2013/0296713 A1    Nov. 7, 2013

Related U.S. Application Data

(63) Continuation of application No. 11/952,940, filed on Dec. 7, 2007, now Pat. No. 8,414,499.

(Continued)

(51) Int. Cl.
*A61B 5/00* (2006.01)
*A61B 5/02* (2006.01)
(Continued)

(52) U.S. Cl.
CPC .......... *A61B 5/0295* (2013.01); *A61B 5/0261* (2013.01); *A61B 5/02416* (2013.01); *A61B 5/14551* (2013.01); *A61B 5/7278* (2013.01)

(58) Field of Classification Search
None
See application file for complete search history.

(56) References Cited

U.S. PATENT DOCUMENTS

| 4,432,374 A | 2/1984 | Osanai |
| 4,867,165 A | 9/1989 | Noller et al. |

(Continued)

FOREIGN PATENT DOCUMENTS

| JP | 2001-321347 A | 11/2001 |
| JP | 2002-028138 A | 1/2002 |

(Continued)

OTHER PUBLICATIONS

Awad et al., Different Responses of Ear and Finger Pulse Oximeter Wave Form to Cold Pressor Test, Anesth Analg 2001, vol. 92, pp. 1483-1486.

(Continued)

*Primary Examiner* — Michael R Bloch
(74) *Attorney, Agent, or Firm* — Knobbe, Martens, Olson & Bear, LLP

(57) ABSTRACT

A plethysmograph variability processor inputs a plethysmograph waveform having pulses corresponding to pulsatile blood flow within a tissue site. The processor derives plethysmograph values based upon selected plethysmograph features, determines variability values, and calculates a plethysmograph variability parameter. The variability values indicate the variability of the plethysmograph features. The plethysmograph variability parameter is representative of the variability values and provides a useful indication of various physiological conditions and the efficacy of treatment for those conditions.

13 Claims, 4 Drawing Sheets

Related U.S. Application Data

(60) Provisional application No. 60/998,782, filed on Oct. 12, 2007, provisional application No. 60/873,663, filed on Dec. 9, 2006.

(51) Int. Cl.
*A61B 5/0295* (2006.01)
*A61B 5/1455* (2006.01)
*A61B 5/024* (2006.01)
*A61B 5/026* (2006.01)

(56) References Cited

U.S. PATENT DOCUMENTS

| | | |
|---|---|---|
| 4,960,128 A | 10/1990 | Gordon et al. |
| 4,964,408 A | 10/1990 | Hink et al. |
| 5,041,187 A | 8/1991 | Hink et al. |
| 5,069,213 A | 12/1991 | Polczynski |
| 5,163,438 A | 11/1992 | Gordon et al. |
| 5,337,744 A | 8/1994 | Branigan |
| 5,341,805 A | 8/1994 | Stavridi et al. |
| D353,195 S | 12/1994 | Savage et al. |
| D353,196 S | 12/1994 | Savage et al. |
| 5,377,676 A | 1/1995 | Vari et al. |
| D359,546 S | 6/1995 | Savage et al. |
| 5,431,170 A | 7/1995 | Mathews |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A | 7/1996 | Kaspari et al. |
| 5,561,275 A | 10/1996 | Savage et al. |
| 5,562,002 A | 10/1996 | Lalin |
| 5,590,649 A | 1/1997 | Caro et al. |
| 5,602,924 A | 2/1997 | Durand et al. |
| 5,613,496 A * | 3/1997 | Arand ............... A61B 5/04525 600/509 |
| 5,632,272 A * | 5/1997 | Diab ................... G06K 9/0051 600/323 |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,685,299 A | 11/1997 | Diab et al. |
| D393,830 S | 4/1998 | Tobler et al. |
| 5,743,262 A | 4/1998 | Lepper, Jr. et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,995,855 A | 11/1999 | Kiani et al. |
| 5,997,343 A | 12/1999 | Mills et al. |
| 6,002,952 A | 12/1999 | Diab et al. |
| 6,011,986 A | 1/2000 | Diab et al. |
| 6,027,452 A | 2/2000 | Flaherty et al. |
| 6,036,642 A | 3/2000 | Diab et al. |
| 6,045,509 A | 4/2000 | Caro et al. |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,124,597 A | 9/2000 | Shehada |
| 6,129,675 A | 10/2000 | Jay |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,321,100 B1 | 11/2001 | Parker |
| 6,325,761 B1 | 12/2001 | Jay |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,385,471 B1 * | 5/2002 | Mortz ........................... 600/323 |
| 6,388,240 B2 | 5/2002 | Schulz et al. |
| 6,397,091 B2 | 5/2002 | Diab et al. |
| 6,430,525 B1 | 8/2002 | Weber et al. |
| 6,463,311 B1 | 10/2002 | Diab |
| 6,470,199 B1 | 10/2002 | Kopotic et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,639,668 B1 | 10/2003 | Trepagnier |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Diab et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,792,300 B1 | 9/2004 | Diab et al. |
| 6,813,511 B2 | 11/2004 | Diab et al. |
| 6,816,741 B2 | 11/2004 | Diab |

(56) References Cited

U.S. PATENT DOCUMENTS

| | | | |
|---|---|---|---|
| 6,822,564 | B2 | 11/2004 | Al-Ali |
| 6,826,419 | B2 | 11/2004 | Diab et al. |
| 6,830,711 | B2 | 12/2004 | Mills et al. |
| 6,850,787 | B2 | 2/2005 | Weber et al. |
| 6,850,788 | B2 | 2/2005 | Al-Ali |
| 6,852,083 | B2 | 2/2005 | Caro et al. |
| 6,861,639 | B2 | 3/2005 | Al-Ali |
| 6,869,402 | B2 | 3/2005 | Arnold |
| 6,898,452 | B2 | 5/2005 | Al-Ali et al. |
| 6,920,345 | B2 | 7/2005 | Al-Ali et al. |
| 6,931,268 | B1 | 8/2005 | Kiani-Azarbayjany et al. |
| 6,934,570 | B2 | 8/2005 | Kiani et al. |
| 6,939,305 | B2 | 9/2005 | Flaherty et al. |
| 6,942,622 | B1 | 9/2005 | Turcott |
| 6,943,348 | B1 | 9/2005 | Coffin, IV |
| 6,950,687 | B2 | 9/2005 | Al-Ali |
| 6,961,598 | B2 | 11/2005 | Diab |
| 6,970,792 | B1 | 11/2005 | Diab |
| 6,979,812 | B2 | 12/2005 | Al-Ali |
| 6,985,764 | B2 | 1/2006 | Mason et al. |
| 6,993,371 | B2 | 1/2006 | Kiani et al. |
| 6,996,427 | B2 | 2/2006 | Ali et al. |
| 6,999,904 | B2 | 2/2006 | Weber et al. |
| 7,003,338 | B2 | 2/2006 | Weber et al. |
| 7,003,339 | B2 | 2/2006 | Diab et al. |
| 7,015,451 | B2 | 2/2006 | Dalke et al. |
| 7,024,233 | B2 | 4/2006 | Ali et al. |
| 7,027,849 | B2 | 4/2006 | Al-Ali |
| 7,030,749 | B2 | 4/2006 | Al-Ali |
| 7,039,449 | B2 | 5/2006 | Al-Ali |
| 7,041,060 | B2 | 5/2006 | Flaherty et al. |
| 7,044,917 | B2 | 5/2006 | Arnold |
| 7,044,918 | B2 | 5/2006 | Diab |
| 7,067,893 | B2 | 6/2006 | Mills et al. |
| 7,096,052 | B2 | 8/2006 | Mason et al. |
| 7,096,054 | B2 | 8/2006 | Abdul-Hafiz et al. |
| 7,132,641 | B2 | 11/2006 | Schulz et al. |
| 7,142,901 | B2 | 11/2006 | Kiani et al. |
| 7,149,561 | B2 | 12/2006 | Diab |
| 7,186,966 | B2 | 3/2007 | Al-Ali |
| 7,190,261 | B2 | 3/2007 | Al-Ali |
| 7,215,984 | B2 | 5/2007 | Diab |
| 7,215,986 | B2 | 5/2007 | Diab |
| 7,221,971 | B2 | 5/2007 | Diab |
| 7,225,006 | B2 | 5/2007 | Al-Ali et al. |
| 7,225,007 | B2 | 5/2007 | Al-Ali |
| RE39,672 | E | 6/2007 | Shehada et al. |
| 7,239,905 | B2 | 7/2007 | Kiani-Azarbayjany et al. |
| 7,245,953 | B1 | 7/2007 | Parker |
| 7,254,431 | B2 | 8/2007 | Al-Ali |
| 7,254,433 | B2 | 8/2007 | Diab et al. |
| 7,254,434 | B2 | 8/2007 | Schulz et al. |
| 7,272,425 | B2 | 9/2007 | Al-Ali |
| 7,274,955 | B2 | 9/2007 | Kiani et al. |
| D554,263 | S | 10/2007 | Al-Ali |
| 7,280,858 | B2 | 10/2007 | Al-Ali et al. |
| 7,289,835 | B2 | 10/2007 | Mansfield et al. |
| 7,292,883 | B2 | 11/2007 | De Felice et al. |
| 7,295,866 | B2 | 11/2007 | Al-Ali |
| 7,328,053 | B1 | 2/2008 | Diab et al. |
| 7,332,784 | B2 | 2/2008 | Mills et al. |
| 7,340,287 | B2 | 3/2008 | Mason et al. |
| 7,341,559 | B2 | 3/2008 | Schulz et al. |
| 7,343,186 | B2 | 3/2008 | Lamego et al. |
| D566,282 | S | 4/2008 | Al-Ali et al. |
| 7,355,512 | B1 | 4/2008 | Al-Ali |
| 7,976,472 | B2 | 7/2011 | Kiani |
| 8,414,499 | B2 | 4/2013 | Al-Ali et al. |
| 2002/0002339 | A1 | 1/2002 | Sugo et al. |
| 2005/0085702 | A1* | 4/2005 | Diab ............... 600/324 |
| 2008/0064965 | A1* | 3/2008 | Jay et al. ......... 600/484 |
| 2008/0079299 | A1* | 4/2008 | Jackson ........... 297/284.4 |

FOREIGN PATENT DOCUMENTS

| | | |
|---|---|---|
| JP | 2002-191569 A | 7/2002 |
| JP | 2006-516000 A | 6/2006 |
| WO | WO 2004/034898 | 4/2004 |
| WO | WO 2004/052196 | 6/2004 |
| WO | WO 2004/080300 | 9/2004 |
| WO | WO 2005/096922 | 10/2005 |
| WO | WO 2005096922 A1 * | 10/2005 |
| WO | WO 2006/097866 | 9/2006 |

OTHER PUBLICATIONS

Awad, et al., How Does the Plethysmogram Derived from the Pulse Oximeter Relate to Arterial Blood Pressure in Coronary Artery Bypass Graft Patients?, The International Anesthesia Research Society, 2001, pp. 1466-1471.

Brian L. Partridge, MD, DPhil., Use of Pulse Oximetry as a noninvasive indicator of intravascular volume status, Journal of Clinical Monitoring 1987 vol. 3 No. 4, pp. 263-268.

Cannesson et al., New Algorithm for Automatic Estimation of the Respiratory Variations in the Pulse Oximeter Waveform in Mechanically Ventilated Patients, Crit Care Med 2007 Abstract vol. 35 No. 12 (Suppl), p. A87.

Cannesson et al., New Algorithm for Automatic Estimation of the Respiratory Variations in the Pulse Oxymeter Waveform, ASA Annual Meeting Abstracts Oct. 13, 2007.

Cannesson et al., New Algorithm for Automatica Estimation of the Respiratory Variations in the Pulse Oximeter Waveform in Spontaneously Breathing Patients, Crit Care Med 2007 Abstract vol. 35 No. 12 (Suppl), p. A87.

Cannesson et al., Relation between respiratory variations in pulse oximetry plethysmographic waveform amplitude and arterial pulse pressure in ventilated patients, Critical Care 2005, 9:R562-R568.

Cannesson et al., Relation between Respiratory Variations in Pulse Oximetry Plethysmographic Waveform Amplitude and Arterial Pulse Pressure in Ventilated Patients: Critical Care, Aug. 23, 2005; 9(5): 562-568.

Cannesson et al., Respiratory variations in pulse oximeter waveform amplitude are influenced by venous return in mechanically ventilated patients under general anaesthesia, European Journal of Anaesthesiology 2007, vol. 24, Paces 245-251.

Cannesson et al., Respiratory Variations in Pulse Oximetry Plethysmographic Waveform Amplitude to Predict Fluid Responsiveness in the Operating Room, Anesthesiology, V 106, No. 6, Jun. 2007, pp. 1105-1111.

Dale W. Steele et al, Pulsus Paradoxus an Objective measure of Severity in Croup, 1998; 157:331-334.

Dell R et al, Direct Measurement of Pulsus Paradoxus in Acute Severe Asthma, Sep. 1996; 150(9):914-8.

Dorlas, J.C. and JA Nijboer (1985) "Photo-electric plethysmography as a monitoring device in anaesthesia. Application and interpretation." British Journal of Anaesthesia 57 (5): 524-30.

Dr. James Rayner et al, Continuous Noninvasive Measurement of Pulsus Paradoxus Complements Medical Decision Making in Assessment of Acute Asthma Severity, 2006; 130:754-765.

Feissel et al., Plethysmographic dynamic indices predict fluid responsiveness in septic ventilated patients, Intensive Care Med (2007) 33, pp. 993-999.

Frey B et al, Pulse Oximetry for Assessment of Pulsus Paradoxus: A Clinical Study in Children, Mar. 1999; 25(3):333-4.

Golparvar et al., Evaluating the Relationship Between Arterial Blood Pressure Changes and Indices of Pulse Oximetric Plethysmography, Anesth Analg 2002 vol. 95, pp. 1686-1690.

Gregory D. Jay et al, Analysis of Physician Ability in the Measurement of Pulsus Paradox by Sphygmomanometry, 2000; 228;348-352.

James D. and R. Brown (1990). "Vascular volume monitoring with pulse oximetry during pediatric anesthesia [correspondence]." Can J Anaesth 37: 266-7.

Jeff A. Clark et al, Comparison of Traditional and Plethysmographic Methods for Measuring Pulsus Paradoxus, Jan. 2004; 158:48-51.

(56) References Cited

OTHER PUBLICATIONS

Jespersen, L. T. and O. Lederballe (1986). "Quantitative photoplethysmography." Surgery 99(1): 130.
Jespersen, L.T. and O.L. Pedersen (1986). "The quantitative aspect of photoplethysmography revised." Heart Vessels 2(3): 186-90.
Kim, J. M., K. Arakawa, et al (1986). "Pulse oximetry and circulatory kinetics associated with pulse volume amplitude measured by photoelectric plethysmography." Anesth Analg 65 (12): 1333-9.
Kirk Shelley M.D., Ph.D., Using the Pulse Oximeter to determine Intravascular Volume Status Non-Invasively, Yale University, School of Medicine, undated PowerPoint presentation, 17 slides.
Lherm. T., T. Chevalier, et al. (1995). "Correlation between plethysmography curve variation (dpleth) and pulmonary capillary wedge pressure (pcwp) in mechanically ventilated patients." British Journal of Anaesthesia Suppl. 1 (74): 41.
Maxime Cannesson, MD. "Use of the Pulse Oximeter Waveform as a Non Invasive Functional Hemodynamic Monitoring". Claude Bernard University, Louis Pradel Hospital, undated Power Point presentation in 44 slides.
Mooser V, Regamey C, Stauffer "Le pouls paradoxal" Schweiz. Rundschau Med. (PRAXIS) 83, Nr. 6 (1994) : pp. 158-162 (with English Abstract).
Murray et al., The Peripheral Pulse Wave: Information Overlooked, Journal of Clinical Monitoring 1996, vol. 12, pp. 365-377.
Natalini et al., Arterial Versus Plethysmographic Dynamic Indices to Test Responsiveness for Testing Fluid Administration in Hypotensive Patients: A Clinical Trial, Anesth Analg Dec. 2006 vol. 103 No. 6, Paces 1478-1484.
Natalini et al., Variations in Arterial Blood Pressure and Photoplethysmography During Mechanical Ventilation, Anesth Analg Nov. 2006 vol. 103 No. 5, pp. 1182-1188.
Paul Barach, MD. "Pulsus Paradoxus". Hospital Physician, Jan. 2000, pp. 49-50.
Pitson DJ et al, Use of Pulse Transit Time as a Measure of Inspiratory Effort in Patients With Obstructive Sleep Apnoea.
Robert F. Tamburro et al, Detection of Pulsus Paradoxus Associated with Large Pericardial Effusions in Pediatric Patients by Analysis of the Pulse-Oximetry Waveform, 2002; 109; 673-677.
Shamir et al., Pulse Oximetry plethysmographic waveform during changes in blood volume, British Journal of Anaesthesia 1999 vol. 82 No. 2, pp. 178-181.
Shelley et al, The Use of Joint Time Frequency Analysis to Quantify the Effect of Ventilation on the Pulse Oximeter Waveform, Journal of Clinical Monitoring and Computing (2006) 20: 81-87.
Shelley et al., What Is the Best Site for Measuring the Effect of Ventilation on the Pulse Oximeter Waveform?, Anesth Analg, Aug. 2006, vol. 103 No. 2, pp. 372-377.
Shelley, et al., Arterial—Pulse Oximetry Loops: A New Method of Monitoring Vascular Tone, Journal of Clinical Monitoring, Jul. 1997, pp. 223-228.
Shelley, et al., Pulse Oximeter Waveform: Photoelectric Plethysmography, in Clinical Monitoring, Carol Lake, R. Hines, and C. Blitt, Eds.: W.B. Saunders Company, 2001, pp. 420-428.
Steele DW et al, Continuous Noninvasive Determination of Pulsus Paradoxus: A Pilot Study, Oct. 1995;8(10):1669-74.
Steele DW et al, Continuous Noninvasive Measurement of Pulsus, Academy Emergency Medicine: Official Journal of the Society for Academic emergency Medicine, 1995, 894-900, 2(10), Hanley & Belfus, Philadelphia, PA.
Steele DW et al, Pulsus Paradoxus: An Objective Measure of Severity in Croup, Nov. 1997; 52(11):1115.
Szecsei, Homework Helpers Basic Math and Pre-Algebra, 2006, The Career Press, p. 133.
Translation of Japanese Office Action in JP App. No. 2009-540509, dated Aug. 23, 2012, 3 pgs.
Wright RO et al, Continuous, Noninvasive Measurement of Pulsus Paradoxus in Patients With Acute Asthma, Oct. 1995;2(10):894-900.
Nolan et al., "Invasive Hemodynamic Monitoring in Obstetrics. A Critical Review of its Indications, Benefits, Complications, and Alternatives", American College of Chest Physicians 101, May 1992, p. 1429-1433. [As previously submitted as Exhibit 1 in the above application's Appeal Brief filed on Feb. 22, 2017].
Vincent et al., "Clinical review: Update on hemodynamic monitoring-a consensus of 16", Critical Care, Aug. 18, 2011, p. 1-8, vol. 15 No. 229. [As previously submitted as Exhibit 3 in the above application's Appeal Brief filed on Feb. 22, 2017].
Pinsky et al., "Functional hemodynamic monitoring", Critical Care, Dec. 2005, p. 566-572, vol. 9 No. 6. [As previously submitted as Exhibit 4 in the above application's Appeal Brief filed on Feb. 22, 2017].
Keller et al., "Ability of pleth variability index to detect hemodynamic changes induced by passive leg raising in spontaneously breathing volunteers", Critical Care, Mar. 6, 2008, p. 1-7, vol. 12 No. 2. [As previously submitted as Exhibit 5 in the above application's Appeal Brief filed on Feb. 22, 2017].
Pleth Variability Index: A Dynamic Measurement to Help Assess Physiology and Fluid Responsiveness, Technical Bulletin, http://www.masimo.co.uk/pdf/pvi/LAB7698A_Technical_Bulletin_Pleth_Variability_Index_British.pdf, 12 pgs, prepared Jun. 13, 2013. [As previously submitted as Exhibit 2 in the above application's Appeal Brief filed on Feb. 22, 2017].

* cited by examiner

PLETHYSMOGRAPH VARIABILITY PROCESSOR

PRIORITY APPLICATIONS

This application is a continuation of U.S. patent application Ser. No. 11/952,940 entitled Plethysmograph Variability Processor, filed Dec. 7, 2007, which claims priority to U.S. Provisional Patent Application No. 60/873,663 filed Dec. 9, 2006, entitled Plethysmograph Variability Index, and U.S. Provisional Patent Application No. 60/998,782 filed Oct. 12, 2007, entitled Plethysmograph Variability Index. All of the above-referenced applications are incorporated by reference herein.

BACKGROUND

Pulse oximetry utilizes a noninvasive sensor to measure oxygen saturation ($SpO_2$) and pulse rate of a person. The sensor has light emitting diodes (LEDs) that transmit optical radiation of red and infrared wavelengths into a tissue site and a detector that responds to the intensity of the optical radiation after attenuation by pulsatile arterial blood flowing within the tissue site. Pulse oximeters have gained rapid acceptance in a wide variety of medical applications, including surgical wards, intensive care and neonatal units, general wards, home care, physical training, and virtually all type of monitoring scenarios.

Pulse oximeters capable of reading through motion induced noise are disclosed in at least U.S. Pat. Nos. 6,770,028, 6,658,276, 6,584,336, 6,263,222, 6,157,850, 5,769,785, and 5,632,272, which are assigned to Masimo Corporation ("Masimo") of Irvine, Calif. and are incorporated by reference herein. Low noise pulse oximetry sensors are disclosed in one or more of U.S. Pat. Nos. 7,027,849, 6,985,764, 6,934,570 6,760,607 6,377,829 6,285,896 5,782, 757 5,638,818, which are also assigned to Masimo and incorporated by reference herein. Moreover, pulse oximeters capable of reading through motion induced noise and low noise optical sensors including LNOP® disposable, reusable and/or multi-site sensors and Radical®, Rad-5™, Rad-8™, Rad9™, PPO+™ monitors are also available from Masimo.

Multiple parameter monitors and multiple wavelength sensors are described in U.S. patent application Ser. No. 11/367,033 entitled Noninvasive Multiple Parameter Patient Monitor filed Mar. 1, 2006 and U.S. patent application Ser. No. 11/367,013 entitled Multiple Wavelength Sensor Emitters filed Mar. 1, 2006, incorporated by reference herein. Moreover, multiple parameter monitors and multiple wavelength sensors including Rad57™ and Radical-7™ monitors and Rainbow™ Rainbow™-brand adhesive and reusable sensors are available from Masimo. MS-brand processor boards incorporating SHARC® DSPs from Analog Devices, Inc. are also available from Masimo.

SUMMARY

An aspect of a plethysmograph variability processor inputs a plethysmograph waveform, derives perfusion values, determines variability values, and calculates a plethysmograph (pleth) variability index. The plethysmograph waveform has pulses corresponding to pulsatile blood flow within a tissue site. The perfusion values correspond to the pulses. The variability values are each indicative of the variability of a series of the perfusion values. The plethysmograph variability index is representative of the variability values. The plethysmograph variability index is displayed.

In various embodiments, the perfusion values are derived by identifying peaks and valleys for the pulses, calculating AC values for the pulses from the peaks and the valleys, calculating DC values for the pulses, and normalizing the AC values with the DC values. Variability values are determined by accumulating the perfusion values in buffers and calculating one of the variability values for each of the buffers. As an example, variability values are determined by sorting the perfusion values within each of the buffers from the largest of the perfusion values to the smallest of the perfusion values and trimming at least one of the largest perfusion values and at least one of the smallest perfusion values from each of the buffers.

Plethysmograph variability indexes (PVIs) are determined from a percentage difference between a maximum perfusion value and a minimum perfusion value for each of the buffers. A median value of the PVIs is calculated. In an embodiment, physiologically acceptable pulses are identified and a minimum amount of time's worth of acceptable data for each buffer is determined. An IR channel is input for the plethysmograph waveform and a red channel is used to verify acceptable pulses.

An aspect of a plethysmograph variability processing system is an optical sensor that transmits multiple wavelengths of optical radiation into a tissue site, detects the optical radiation after attenuation by pulsatile blood flowing within the tissue site, and generates a sensor signal responsive to the detected optical radiation. A patient monitor demodulates the sensor signal so as to generate a plethysmograph channels. A digital signal processor (DSP) within the patient monitor inputs at least one of the plethysmograph channels and outputs a plethysmograph variability (PV) parameter accordingly. A PV process executes on the DSP so as to process the plethysmograph channel and derive the PV parameter. A patient monitor output is responsive to the PV parameter.

In various embodiments, the PV process has a plethysmograph input corresponding to the at least one plethysmograph channel. The pleth has pleth features. A measure pleth process extracts the pleth values from the plethysmograph according to the pleth features. A pleth value input corresponds to the pleth values. A pleth variability process generates a plurality of variability values from the pleth values. A pleth variability input corresponds to the variability values. A variability parameter process generates a pleth variability (PV) parameter from the variability values. Physiological acceptability criteria are applied to the plethysmograph input. A reduce data dispersion process trims outlying ones of the pleth values according to dispersion criteria. Post processing applies at least one of a smoothing or slew rate limit to the PV parameter. Pre-processing applies a bandpass filter to the plethysmograph input so as to remove a cyclical baseline shift or oscillation from the plethysmograph. The patient monitor output generates a graph of the PV parameter versus time so as to indicate a trend in plethysmograph variability.

An aspect of a plethysmograph variability method inputs plethysmograph channels, measures pleth values from the input and defines windows each encompassing a unique time interval of the plethysmograph values. Variability values are calculated, where each of the variability values are derived from the plethysmograph values encompassed in a unique one of the windows. Second windows are defined, each encompassing a unique time interval of the variability values. Parameter values are calculated, where each of the parameter values are derived from the variability values encompassed in a unique one of the second windows.

Parameter values are output. In various embodiments, the plethysmograph channels each have pulses corresponding to pulsatile blood flow within a tissue site, and the plethysmograph values are based upon the pulses. The plethysmograph values are measures of blood perfusion at the tissue site. In alternative embodiments, plethysmograph values are based upon area under absorption pulses, an envelope of the pulses, a time series of normalized envelope heights or a time series of normalized envelope areas.

An aspect of a plethysmograph variability processing system has a sensor that transmits multiple wavelengths of optical radiation into a tissue site and that detects the optical radiation after attenuation by pulsatile blood flow within a tissue site so as to provide a plethysmograph input to a digital signal processor (DSP). The input is selected from channels corresponding to the multiple wavelengths. The DSP executes instructions for deriving plethysmograph variability from the plethysmograph. A measuring means generates plethysmograph values from the plethysmograph input according to predefined plethysmograph features. A calculation means derives variability values from the plethysmograph values, and a reduction means deriving a plethysmograph variability (PV) parameter from the plethysmograph values. In various embodiments, a first accumulation means applies a variability formula to a window of plethysmograph values. A dispersion reduction means trims outlying values from the first accumulation means. A second accumulation means applies data reduction criteria to a window of variability values. An acceptance means eliminates pulses from the plethysmograph input that are not physiologically acceptable. A post-processing means limits the slope of the PV parameter.

DETAILED DESCRIPTION

PV Monitor

Figure 1:
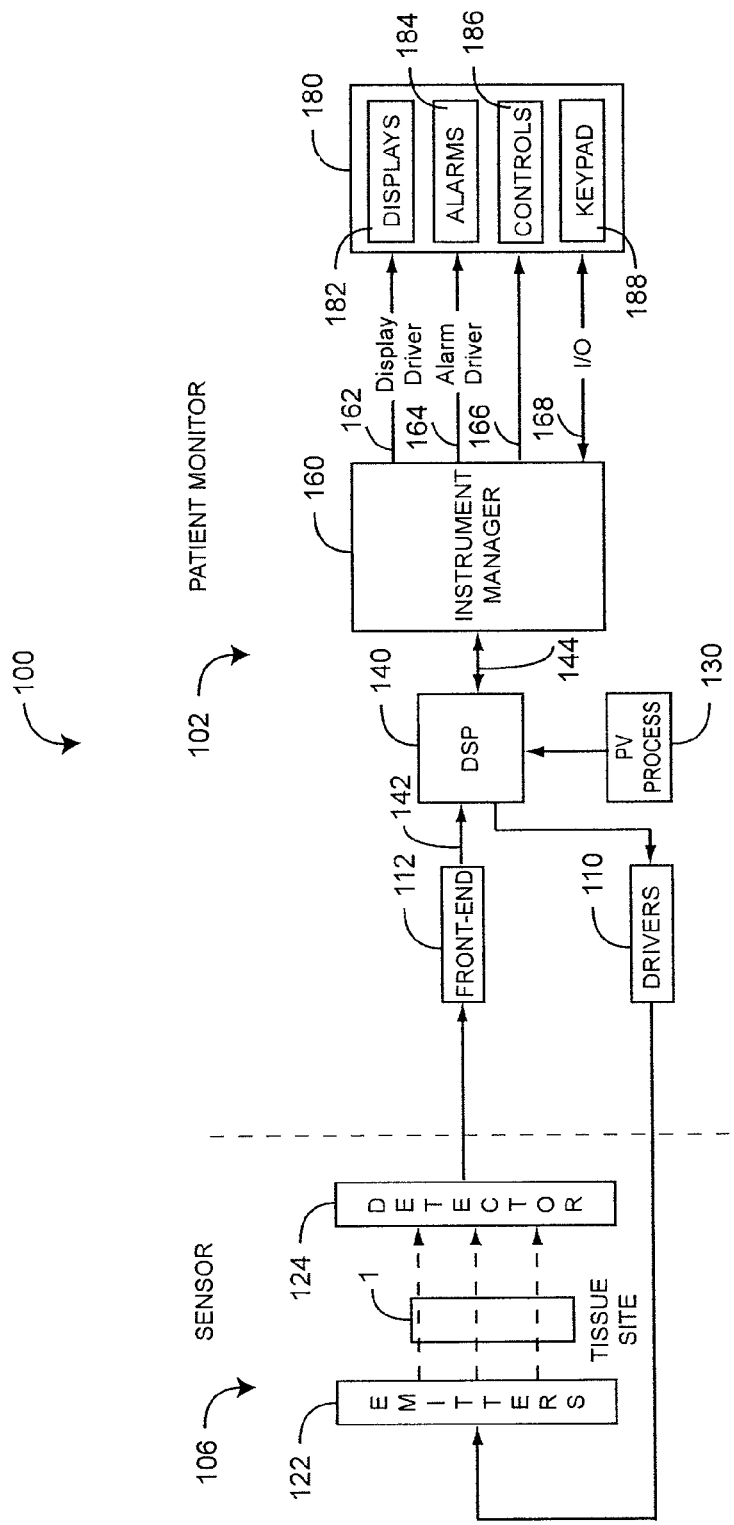
FIG. 1 is a general block diagram of a plethysmograph variability processing system.

FIG. 1 illustrates a plethysmograph variability processing system 100 embodiment, which calculates one or more measures of plethysmograph variability (PV). The plethysmograph variability processing system 100 advantageously provides at least some of displays, alarms or controls responsive to PV so as to indicate, and affect the treatment of, a patient condition. The PV processing system 100 may further generate SpO$_2$, pulse rate (PR), perfusion index (PI), signal quality and in multiple wavelength configurations additional blood parameter measurements such as HbCO and HbMet.

As shown in FIG. 1, the PV processing system 100 has a patient monitor 102 and a sensor 106. The sensor 106 attaches to a tissue site 1 and includes a plurality of emitters 122 capable of irradiating the tissue site 1 with at least two wavelengths of light, such as the red and infrared (IR) wavelengths utilized in pulse oximeters and in some configurations multiple wavelengths different than or in addition to those red and IR wavelengths. The sensor 106 also includes one or more detectors 124 capable of detecting the light after attenuation by the tissue 1.

Also shown in FIG. 1, the patient monitor 102 communicates with the sensor 106 to receive one or more intensity signals indicative of one or more physiological parameters and displays the parameter values. Drivers 110 convert digital control signals into analog drive signals capable of driving sensor emitters 122. A front-end 112 converts composite analog intensity signal(s) from light sensitive detector(s) 124 into digital data 142 input to the DSP 140. The input digital data 142 is referred to herein as a plethysmograph waveform, plethysmograph or pleth for short. The digital data 142 has plethysmograph channels corresponding to each emitter wavelength, such as a red channel and an IR channel. The digital data 142 is representative of a change in the absorption of particular wavelengths of light as a function of the changes in body tissue resulting from pulsing blood. The DSP 140 may comprise a wide variety of data and/or signal processors capable of executing programs for determining physiological parameters from input data. In an embodiment, the DSP executes one or more pleth variability (PV) processes 130, such as described with respect to FIGS. 3-4, below. In an embodiment, the PV processes 130 may be implemented in software, firmware or other form of code or instructions, or logic or other hardware, or a combination of the above.

Further shown in FIG. 1, the instrument manager 160 may comprise one or more microcontrollers controlling system management, such as monitoring the activity of the DSP 140. One or more output devices 180 include displays 182, alarms 184 and controls 186. Displays 182 may be numerical, such as readouts, or graphical, such as trends and bar graphs, generated by LEDs, LCDs or CRTs to name a few. Displays 182 may also be indicators, such as LEDs of various colors that signify variability magnitude. Alarms 184 may be visual or audible indications that variability is, say, above a predetermined threshold. Controls 186 may be inputs to medical equipment, such as drug administration devices, ventilators and fluid IVs, so as to control the amount of administered drugs, ventilator settings or the amount of infused fluids based up pleth variability. The instrument manager 160 also has an input/output (I/O) port 168 that provides a user and/or device interface for communicating with the monitor 102. User input devices 188 may include a keypad, touch screen, pointing device, voice recognition device, network and computer, to name a few. In an embodiment, the I/O port 168 provides initialization settings for PV processes, as described below. The monitor 102 may also be capable of storing or displaying historical or trending data related to PV and other measured parameters or combinations of measured parameters.

Pleth Waveform

Figure 2:
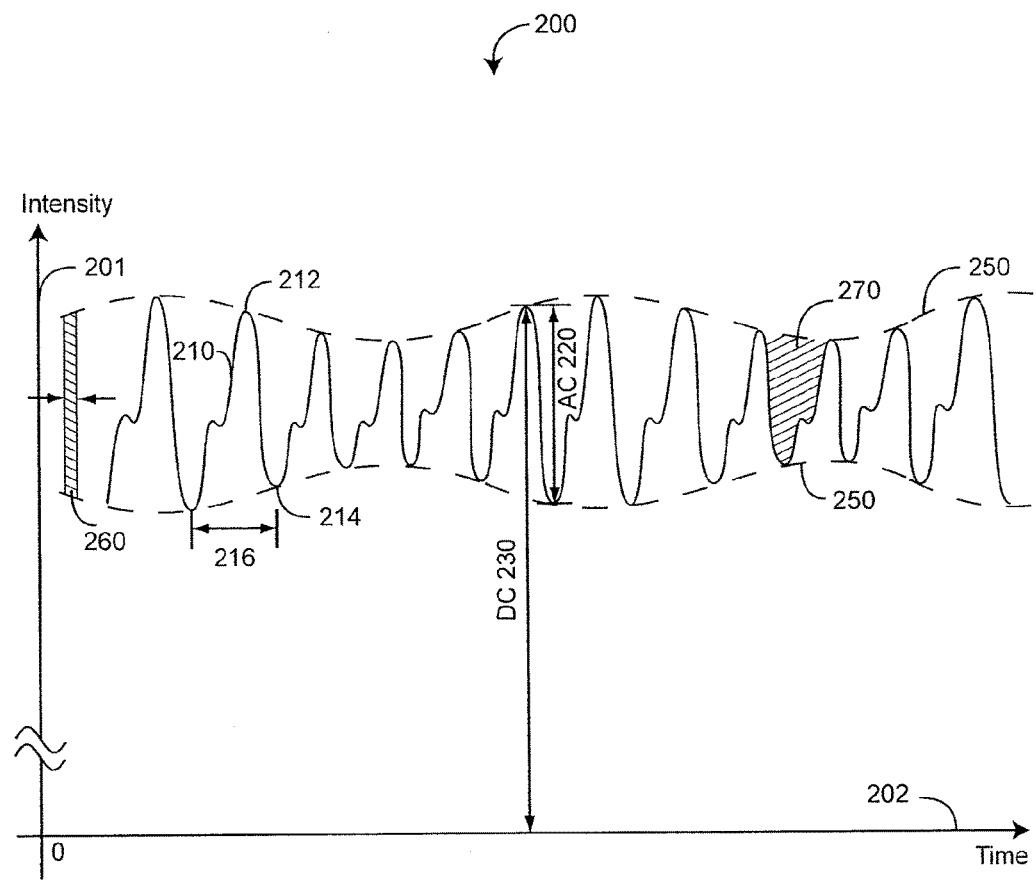
FIG. 2 is a graph of an exemplar plethysmograph.

FIG. 2 illustrates a plethysmograph 200 plotted on an intensity axis 201 versus a time axis 202. The plethysmograph 200 has multiple pulses 210 each with a peak 212 and a valley 214 and extending over a time period 216. A perfusion index (PI) value can be defined for each pulse 210:

$$PI = \frac{AC}{DC} \qquad (1)$$

"AC" 220 designates a peak amplitude 212 minus a valley amplitude 214 for a particular pulse. "DC" 230 designates a peak amplitude 212 for a particular pulse. A plethysmograph variability measure is calculated that is responsive to the magnitude of pleth variations, such as depicted by envelope 250. One variability measure is a plethysmograph variability index (PVI), described with respect to FIG. 3, below. Other plethysmograph variability (PV) measures are described with respect to FIG. 4, below. Advantageously, PV measures may provide a numerical indication of a person's physical condition or health.

Pleth Variability Index (PVI)

Figure 3:
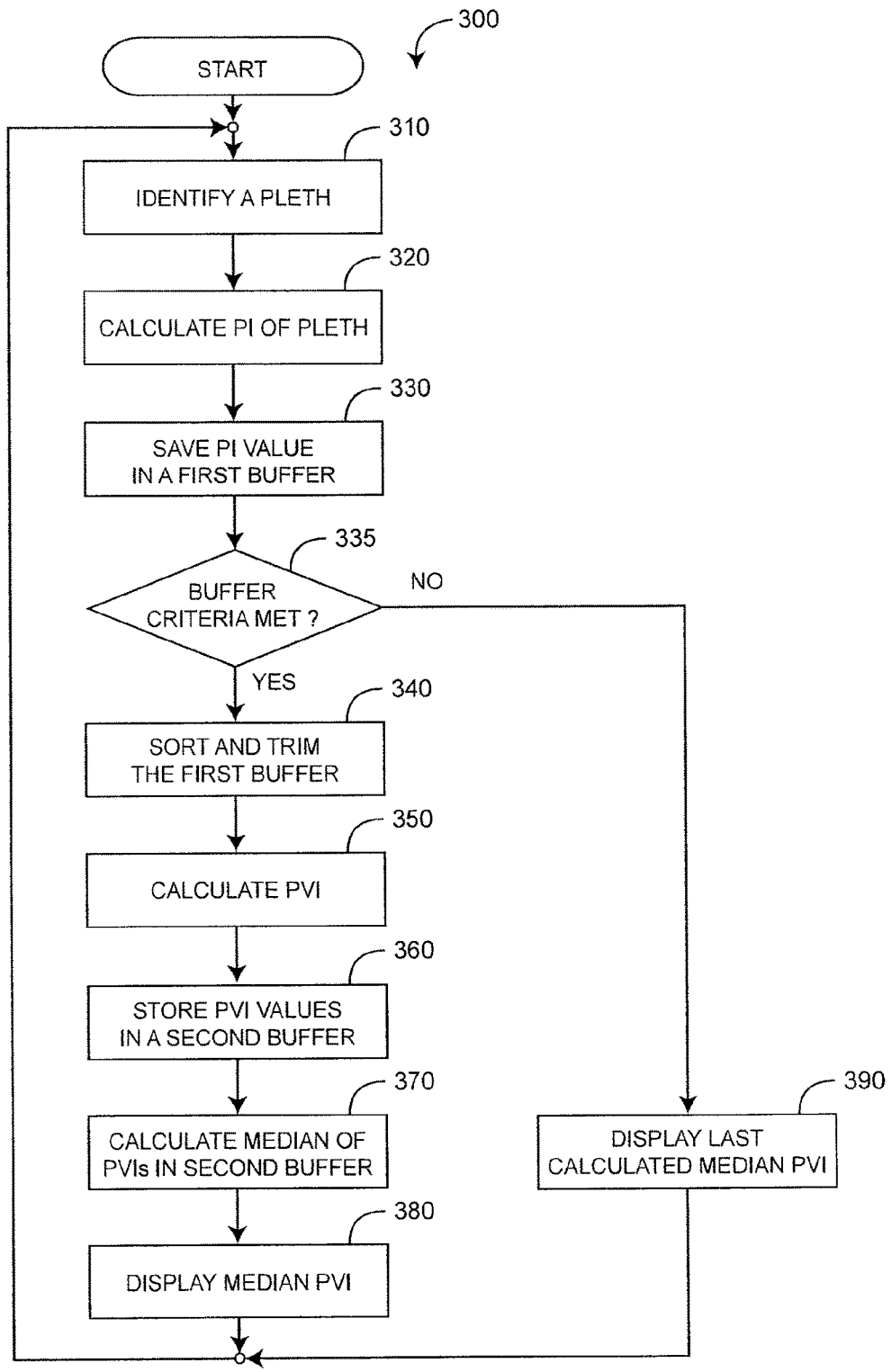
FIG. 3 is a detailed flow chart of a plethysmograph variability index process.

FIG. 3 illustrates a PVI process 300 embodiment, which derives and displays a plethysmograph variability index (PVI). Initially, a first buffer is filled with calculated perfusion index (PI) values 310-330. In an embodiment, these values are based upon the IR channel, as described above. If a sufficient amount of physiologically acceptable data is in the first buffer 335, then a second buffer is filled with calculated plethysmograph variability index (PVI) values 340-360. The median PVI in the second buffer is calculated and displayed 370-380. If the amount of acceptable data in the first buffer is insufficient, then the display is frozen with the last calculated median PVI 390.

As shown in FIG. 3, a plethysmograph is first identified 310. In particular, only physiologically acceptable pulses are used for calculating PI. Physiological plethysmograph identification is disclosed in U.S. Pat. No. 7,044,918 entitled Plethysmograph Pulse Recognition Processor, which is assigned to Masimo and incorporated by reference herein. In an embodiment, the red channel plethysmograph is utilized to verify acceptable pulses in the IR channel. The PI of each acceptable plethysmograph is then calculated 320 according to EQ. 1 and as described with respect to FIG. 2, above. The calculated PIs are stored in a first buffer 330, and the buffer criteria are tested 335. The buffer criteria require both a minimum number of acceptable pulses and a minimum amount of time of acceptable data in the first buffer.

In an embodiment, a plethysmograph 200 (FIG. 2) has a 62.5 Hz sample rate, i.e. a sample interval of 16 msec. The first buffer holds 15 sec. of data at that sample rate. Accordingly, a sliding 15 sec. window of plethysmograph data is stored in the first buffer, and the window is moved in 1.2 sec. increments. The minimum number of acceptable pulses in the first buffer is 6, and the minimum amount of acceptable data in the first buffer is 7.5 sec. The 15 sec. window size allows one respiration cycle, assuming a worse case respiration rate of 4 breaths per min. This window size also allows 6 PIs assuming a worse case pulse rate of 25 bpm. Partial plethysmograph cycles cutoff by a particular window are ignored by that window, but are taken into account in the next window.

Also shown in FIG. 3, if the buffer criteria are met 335, then the first buffer is sorted and trimmed 340. The sort orders the PI values from the minimum PI at one end of the buffer to the maximum PI at the other end of the buffer. Then a predetermined number of PIs are dropped from each end of the buffer, i.e. both the maximum PIs and the minimum PIs are deleted. In an embodiment, 12% of the PIs are trimmed from each end of the buffer. For example, if the buffer holds 10 PIs, a 12% trim=floor(10·12/100)= floor(1.2)=1, where the floor operator truncates digits to the right of the decimal point. Hence, in this example, one max PI and one min PI are dropped from the first buffer. A plethysmograph variability index (PVI) is then calculated 350 from the trimmed first buffer. In an embodiment, PVI is calculated as:

$$PVI = \frac{PI_{MAX} - PI_{MIN}}{PI_{MAX}} \times 100 \qquad (2)$$

That is, PVI is the PI variation, expressed as a percentage of the maximum PI, reflected by the PI values remaining in the first buffer.

Further shown in FIG. 3, calculated PVIs are stored in a second buffer 360. In an embodiment, the second buffer holds 11 PVIs, where one PVI is derived for every 1.2 sec shift in the sliding 15 sec. window described above. Next, the median PVI is calculated from the second buffer. This median PVI value is communicated to a display 380. If the buffer criteria 335, described above, are not met, then the last calculated median PVI value is displayed 390. That is, the display is frozen with that last calculated median PVI value until the buffer criteria are satisfied.

In an embodiment, the median PVI value is displayed as a two-digit numerical value on a monitor screen along with other parameters, such as $SpO_2$ and pulse rate. In an embodiment, the median PVI value is displayed on a monitor screen as vertical or horizontal bar graph. In an embodiment, the median PVI value is displayed on a monitor screen as trend graph versus time. In an embodiment, the median PVI value is compared to a predetermined maximum PVI threshold. If the median PVI value crosses the predetermined threshold, one or more visual or audible alarms are triggered. In an embodiment, a visual PVI alarm is one or more colored indicators, such as green, yellow and red, indicating levels of patient health or physiological condition.

Plethysmograph Variability (PV)

Figure 4:
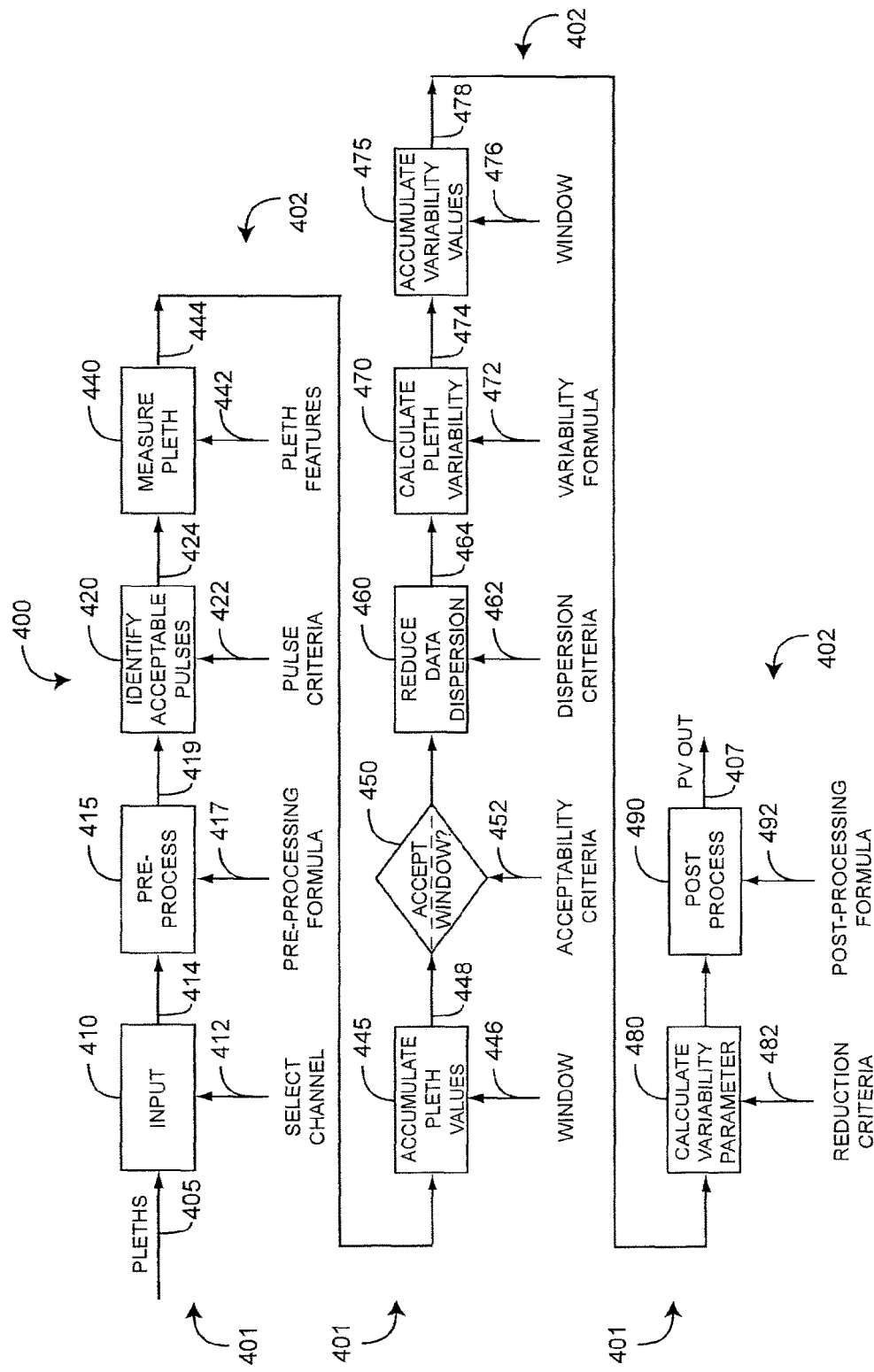
FIG. 4 is a general functional flow diagram of a plethysmograph variability process.

FIG. 4 illustrates a plethysmograph variability (PV) processor 400 embodiment having process steps 401 and initializations 402. The initializations 402 determine the specific characteristics of the process steps 401. The PV processor 400 inputs one or more plethysmograph (pleth) channels 405 and generates PV outputs 407. The pleth channels 405 each correspond to a different optical sensor wavelength, such as a red wavelength channel and an IR wavelength channel corresponding to red and IR emitters of a pulse oximeter sensor. There may be more than two channels when using a multiple wavelength sensor, such as described in U.S. patent application Ser. No. 11/367,013, cited above. For example, there may be eight channels varying in wavelength from about 630 nm to about 905 nm. In an embodiment, two or more pleth channels 405 are processed in parallel or combined as a composite pleth for increased accuracy or robustness in PV calculations. Input 410 determines which pleth channel 405 is used as the pleth input 414 for PV calculations, according to a select channel initialization 412. Input 410 may select any single channel 405 or some combination of channels 405. Pre-process 415 modifies the pleth input 414 according to a predetermined formula 417. In an embodiment, pre-process 415 filters the pleth input 414 so as to remove any slow variation or low frequency oscillation in the plethysmograph baseline or average value, such as a respiration-induced variation that shifts the entire plethysmograph up and down with inhalation and exhalation. In an embodiment, pre-process 415 is a bandpass filter having a 30 to 550 beats per minute passband. Identify acceptable pulses 420 applies pulse criteria 422 to pass only physiologically acceptable pulses 424, such as disclosed in U.S. Pat. No. 7,044,918 cited above.

As shown in FIG. 4, measure pleth 440 extracts pleth values 444 from the remaining pulses 424 according to pleth features 442. The pleth features 434 may be a pulse peak 212 (FIG. 2) and pulse valley 214 (FIG. 2) and the pleth values 444 may relate to perfusion, such as PI described with respect to EQ. 1 above. In another embodiment, the "DC" value in EQ. 1 may be other than a pulse peak, such as a pulse valley or an average of pulse peak and pulse valley, to name a few. In other embodiments, pleth features 442 may include more that two values per pulse and pleth values 444 may be other than perfusion related. Also, measure pleth 440 may be performed over more than one pulse per pleth value 444.

As shown in FIGS. 2 and 4, in an embodiment, pleth features 442 define a pleth envelope 250 interpolated from pulse peaks 212 and pulse valleys 214. Measure pleth 440 defines a series of adjacent slices 260 of envelope height and Δ width, where Δ may vary from one pleth sample to many samples. Accordingly, pleth values 444 are the areas of each slice. In another embodiment, measure pleth 440 calculates the area under each absorption pleth pulse 270, the absorption pleth being the inverse of the intensity pleth 200. In an embodiment, the slices 260 or areas 270 are normalized with respect to a pleth value, such as a DC value or an average value, to name a few.

Also shown in FIG. 4, accumulate pleth values 445 identifies those pleth values 444 within a specified window 446. Accept window 450 determines whether there are a sufficient number of pleth values within the window 446. If not, the remaining steps 460-490 are bypassed and a default PV output 407 is generated. If so, the remaining steps 460-490 are performed. Reduce data dispersion 460 eliminates outlying data, leaving trimmed pleth values 464, according to a dispersion criteria 462. Calculate pleth variability 470 determines a variability value 474 from the trimmed pleth values 464 according to a variability formula 472. In an embodiment, the variability formula is the percentage variability in a window compared with a maximum value in the window, such as described with respect to EQ. 2, above. Accumulate variability values 475 identifies those variability values 474 within a specified window 476. Windows 446, 476 are sliding time intervals or segments having predetermined sizes according to an initialization 402. Adjacent windows may be spaced apart, abutting or overlapping in time.

Further shown in FIG. 4, calculate variability parameter 480 determines a pleth variability (PV) parameter 407 from the accumulated variability values 478 according to a reduction criteria 482. In an embodiment, PV 407 is a median of the variability values 478 in the window 476. In other embodiments, PV 407 is any of average, mode, geometric mean or weighted mean of the windowed variability values, to name a few. Post processing on the PV parameter 407 data may be performed including smoothing and a slew rate filter. In an embodiment, an exponential smoothing is used. The slew rate filter limits the positive or negative slope of the PV parameter 407 to a predetermined maximum.

PV Applications

Many clinicians currently observe a pulse oximeter plethysmograph waveform for changes in patient physiology. Unfortunately, there is no consistency among pulse oximeter manufacturers in the way a plethysmograph waveform is displayed. Further, smoothing, autoscaling and other display data processing mask changes in the raw plethysmograph waveform. Thus, some patient physiology cannot be readily predicted from mere observation of a bedside monitor plethysmograph display. Pleth variability (PV) parameters, such as PVI, advantageously quantify plethysmograph waveform variations, which are displayed in a numerical format that can also be trended as needed. Accordingly, even slight changes in physiology may be reliably observed.

PV can be advantageously used for noninvasive functional hemodynamic monitoring. A plethysmograph waveform is responsive to beat-to-beat changes in peripheral blood volume and perfusion. Thus, plethysmograph variability reflects changes in the intravascular volume status of patients. PV parameters, as described above, are clinically useful hemodynamic measurements that respond to changes in, for example, volemia, fluid responsiveness and ventricular preload. Volemia relates to the volume of blood circulating throughout the body, which is difficult to estimate in a clinical setting. Hypovolemia, for example, is an abnormally low blood volume. Fluid responsiveness is the percent increase in ventricular stroke volume after fluid volume expansion. Ventricular preload is the degree of tension in the cardiac muscle when it begins to contract.

In particularly advantageous embodiments, a PV parameter is monitored during patient treatments. As an example, a downward trend in PV monitored during the addition of fluids to a suspected hypovolemic patient indicates the efficacy of that treatment. Likewise, a downward trend in PV monitored during administration of drugs for asthma indicates the efficacy of the administered drug and the likelihood that the asthma can be controlled.

PVI or other pulse variability (PV) measure may be a significant parameter in a variety of critical conditions, for example those conditions shown in Table 1, below.

TABLE 1

Conditions Associated with Increased PV

| Cardiac Causes | Non-Cardiac Causes |
| --- | --- |
| Cardiogenic Shock | Hypovolemia |
| Cardiac Tamponade | Septic Shock |
| Pericardial Effusion | Anaphylactic Shock |
| Constrictive Pericarditis | Superior Vena Cava Obstruction |
| Restrictive Cardiomyopathy | Asthma |
| Acute myocardial infarction | |

A plethysmograph variability processor has been disclosed in detail in connection with various embodiments. These embodiments are disclosed by way of examples only and are not to limit the scope of the claims that follow. One of ordinary skill in art will appreciate many variations and modifications.

What is claimed is:

1. A computerized method of determining plethysmograph variability in a non-invasive electronic patient monitor using a signal processor comprising:

converting digital control signals into analog drive signals;

causing a sensor emitter to emit a plurality of wavelengths of light by communicating the analog drive signals to the sensor emitter;

receiving a sensor signal from a sensor detector in response to attenuation by pulsatile blood flow within a tissue site;

demodulating the sensor signal to generate a plethysmograph waveform having pulses corresponding to the pulsatile blood flow within the tissue site;

determining a plurality of perfusion values corresponding to the pulses, wherein said determining the plurality of perfusion values comprises:

identifying peaks and valleys of the pulses, and calculating differential values for the pulses from the peaks and the valleys of the pulses, wherein the differential values comprise a difference between the peaks and the valleys of the pulses;

storing a first series of perfusion values of the plurality of perfusion values in a first buffer;

sorting the first series of perfusion values within the first buffer from a largest perfusion value to a smallest perfusion value;

removing at least two perfusion values from the first series of perfusion values to form a modified first series of perfusion values, wherein at least one perfusion value is removed from a set of largest perfusion values of the first series of perfusion values, and at least one perfusion value is removed from a set of smallest perfusion values of the first series of perfusion values;

determining a first variability value indicative of variability of the modified first series of perfusion values based on a difference between a first perfusion value of the modified first series of perfusion values and a second perfusion value of the modified first series of perfusion values and a normalization of the difference with the first perfusion value of the modified first series of perfusion values;

storing a second series of perfusion values of the plurality of perfusion values in a second buffer;

sorting the second series of perfusion values within the second buffer from a largest perfusion value to a smallest perfusion value;

removing at least one perfusion value from a set of largest perfusion values of the second series of perfusion values and at least one perfusion value from a set of smallest perfusion values of the second series of perfusion values to form a modified second series of perfusion values;

determining a second variability value indicative of variability of the modified second series of perfusion values based on a difference between a first perfusion value of the modified second series of perfusion values and a second perfusion value of the modified second series of perfusion values and a normalization of the difference with the first perfusion value of the modified second series of perfusion values;

determining a plethysmograph variability parameter representative of at least the first variability value and the second variability value; and causing a display device to display the plethysmograph variability parameter.

2. The computerized method of claim 1, wherein said determining the plurality of perfusion values further comprises normalizing the calculated differential values.

3. The computerized method of claim 1, wherein said determining the first variability value and the second variability value further comprises calculating a plurality of plethysmograph variability indices from a percentage difference between a maximum perfusion value and a minimum perfusion value for each of the modified first series of perfusion values and the modified second series of perfusion values.

4. The computerized method of claim 3, wherein said determining the plethysmograph variability parameter comprises calculating a median value of the plurality of plethysmograph variability indices.

5. The computerized method of claim 4, further comprising:
identifying physiologically acceptable pulses from the pulses, wherein the pulses comprise physiologically acceptable pulses and physiologically unacceptable pulses; and
determining a minimum amount of time of acceptable data in each of the first buffer and the second buffer.

6. The computerized method of claim 5, further comprising:
verifying the physiologically acceptable pulses using a red channel,
wherein said receiving the sensor signal comprises using an IR channel.

7. A plethysmograph variability system comprising:
a sensor that emits optical radiation and detects the optical radiation after attenuation by pulsatile blood flowing within a tissue site,
a processor in communication with the sensor, the processor configured to execute one or more instructions that cause the processor to:
convert digital control signals into analog drive signals,
cause the sensor to emit the optical radiation by communicating the analog drive signals to the sensor,
receive a sensor signal from the sensor in response to the detected optical radiation after the attenuation,
demodulate the sensor signal to generate a plethysmograph waveform having pulses corresponding to the pulsatile blood flowing within the tissue site,
determine a plurality of perfusion values of pulses corresponding to the pulsatile blood flowing within the tissue site, wherein to determine the plurality of perfusion values the processor is further configured to:
identify peaks and valleys of the pulses, and
calculate differences for the pulses from the peaks and the valleys of the pulses;
store a first series of perfusion values of the plurality of perfusion values in a first buffer;
sort the first series of perfusion values within the first buffer from a largest perfusion value to a smallest perfusion value;
remove at least two perfusion values from the first series of perfusion values to form a modified first series of perfusion values, wherein at least one perfusion value is removed from a set of largest perfusion values of the first series of perfusion values and at least one perfusion value is removed from a set of smallest perfusion values of the first series of perfusion values;
determine a first variability value indicative of variability of the modified first series of perfusion values based on a difference between a first perfusion value of the modified first series of perfusion values and a second perfusion value of the modified first series of perfusion values and a normalization of the difference with the first perfusion value of the modified first series of perfusion values;
store a second series of perfusion values of the plurality of perfusion values in a second buffer;
sort the second series of perfusion values within the second buffer from a largest perfusion value to a smallest perfusion value;
remove at least one perfusion value from a set of largest perfusion values of the second series of perfusion values and at least one perfusion value from a set of smallest perfusion values of the second series of perfusion values to form a modified second series of perfusion values;
determine a second variability value indicative of variability of the modified second series of perfusion values based on a difference between a first perfusion value of the modified second series of perfusion values and a second perfusion value of the modified second series of perfusion values and a normalization of the difference with the first perfusion value of the modified second series of perfusion values;

determine a plethysmograph variability parameter representative of at least the first variability value and the second variability value; and cause a display to display the plethysmograph variability parameter.

8. The system of claim 7, wherein to determine the plurality of perfusion values, the processor is further configured to normalize the calculated differences for the pulses.

9. The system of claim 8, wherein to determine the first variability value and the second variability value, the processor is further configured to calculate a plurality of plethysmograph variability indices from a percentage difference between a maximum perfusion value and a minimum perfusion value for each of the modified first series of perfusion values and the modified second series of perfusion values.

10. The system of claim 9, wherein to determine the plethysmograph variability parameter the processor is configured to calculate a median value of the plurality of plethysmograph variability indices.

11. The system of claim 10, wherein the processor is further configured to:
identify physiologically acceptable pulses from the pulses, wherein the pulses comprise physiologically acceptable pulses and physiologically unacceptable pulses; and
determine a minimum amount of time of acceptable data in each of the first buffer and the second buffer.

12. A computerized method for determining a plethysmograph variability parameter using a signal processor, the computerized method comprising:
converting digital control signals into analog drive signals;
causing a sensor emitter to emit a plurality of wavelengths of light by communicating the analog drive signals to the sensor emitter;
receiving a sensor signal from a sensor detector in response to attenuation by pulsatile blood flow within a tissue site;
demodulating the sensor signal to generate a plethysmograph waveform having pulses corresponding to the pulsatile blood flow within the tissue site;
identifying relative minimums and relative maximums of the pulses;
calculating differences for the pulses from the identified relative minimums and relative maximums of the pulses to determine a plurality of perfusion values for the pulses, wherein the plurality of perfusion values comprise at least a first set of perfusion values and a second set of perfusion values;

storing the first set of perfusion values in a first buffer;
sorting the first set of perfusion values within the first buffer from a largest perfusion value to a smallest perfusion value;
removing at least two perfusion values from the first set of perfusion values to form a modified first set of perfusion values, wherein one perfusion value is removed from a set of largest perfusion values of the first series of perfusion values and at least one perfusion value is removed from a set of smallest perfusion values of the first series of perfusion values;
calculating a variability value of the modified first set of perfusion values using at least a normalized difference between a first perfusion value of the modified first set of perfusion values and a second perfusion value of the modified first set of perfusion values, wherein the difference is normalized with respect to the first perfusion value of the modified first set of perfusion values;
storing the second set of perfusion values in a second buffer;
sorting the second set of perfusion values within the second buffer from a largest perfusion value to a smallest perfusion value;
removing at least two perfusion values from the second set of perfusion values to form a modified second set of perfusion values, wherein one perfusion value is removed from a set of largest perfusion values of the second set of perfusion values and at least one perfusion value is from a set of smallest perfusion values of the second set of perfusion values;
calculating a variability value of the modified second set of perfusion values using at least a normalized difference between a first perfusion value of the modified second set of perfusion values and a second perfusion value of the modified second set of perfusion values, wherein the difference is normalized with respect to the first perfusion value of the modified second set of perfusion values;
determining a plethysmograph variability parameter representative of at least the variability value of the modified first set of perfusion values and the variability value of the modified second set of perfusion values; and
causing a display device to display the plethysmograph variability parameter.

13. The computerized method of claim 12, further comprising normalizing the calculated differences to determine the plurality of perfusion values.

* * * * *